United States Patent [19]

Maier et al.

[11] 4,379,784
[45] Apr. 12, 1983

[54] PYRIMIDINYL UREIDO PENICILLINS

[75] Inventors: Roland Maier; Bernd Wetzel; Eberhard Woitun, all of Biberach; Wolfgang Reuter, Laupertshausen; Uwe Lechner, Ummendorf; Hanns Goeth, Biberach, all of Fed. Rep. of Germany

[73] Assignee: Dr. Karl Thomae Gesellschaft mit beschränkter Haftung, Biberach an der Riss, Fed. Rep. of Germany

[21] Appl. No.: 323,383

[22] Filed: Nov. 20, 1981

[30] Foreign Application Priority Data

Dec. 5, 1980 [DE] Fed. Rep. of Germany ....... 3045908
Dec. 12, 1980 [DE] Fed. Rep. of Germany ....... 3046839

[51] Int. Cl.³ ................ A61K 31/505; A61K 31/635; C07D 499/70
[52] U.S. Cl. .............................. 424/229; 260/239.1; 260/239.75; 424/246; 424/248.51; 424/251; 544/321
[58] Field of Search ..................... 260/239.1; 424/251, 424/246, 248.51, 229

[56] References Cited

U.S. PATENT DOCUMENTS 3,308,023 3/1967 Russell ............................. 260/239.1
3,352,851 11/1967 Fosker ............................. 260/239.1
4,038,271 7/1977 Breuer et al. .................... 260/239.1

Primary Examiner—Natalie Trousof
Assistant Examiner—Vera C. Clarke
Attorney, Agent, or Firm—Hammond, Littell, Weissenberger & Muserlian

[57] ABSTRACT

Compounds of the formula where $R_1$ and $R_2$, which may be identical to or different from each other, are each methylmercapto or amino;

$Z'$ is oxygen, sulfur or $=NR_3$;

$R_3$ is hydrogen, alkyl of 1 to 3 carbon atoms or hydroxy-(alkyl of 1 to 3 carbon atoms);

$R_4$ is hydrogen, hydroxyl, hydroxymethyl or methyl;

n is 2, 3 or 4;

Y is $-SO_2NH-$, $-SO-$ or $-SO_2-$;

Z is straight or branched alkylene of 1 to 3 carbon atoms;

X is hydroxyl, aminocarbonyl, aminosulfonyl, formylamino, acetylamino, amino, methylsulfinyl, methylsulfonyl or $-CH\begin{subarray}{l}NH_2\\COOH\end{subarray}$ ; or or $-Y-Z-X$ is and non-toxic, pharmacologically acceptable salts thereof formed with inorganic or organic bases. The compounds as well as the salts are useful as antibiotics.

wherein
  A is phenyl, 4-hydroxy-phenyl, 2-thienyl or 3,4-dihydroxy-phenyl; and
  R is 8 Claims, No Drawings

PYRIMIDINYL UREIDO PENICILLINS

This invention relates to novel penicillins and salts thereof, to methods of preparing these compounds, to pharmaceutical compositions containing them as active ingredients, and to a method of using them as antibiotics.

More particularly, the present invention relates to a novel class of penicillins represented by the tautomeric formulas

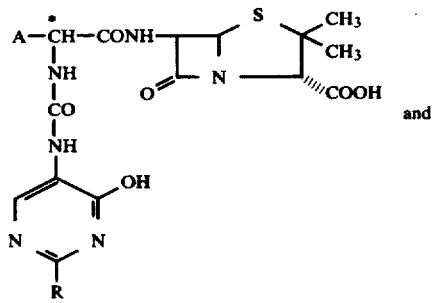

and

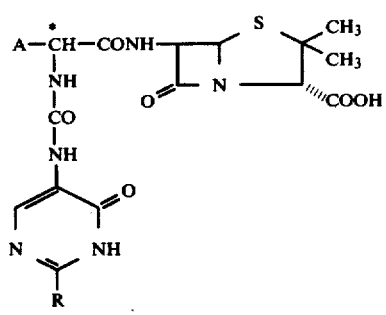

wherein
A is phenyl, 4-hydroxy-phenyl, 2-thienyl or 3,4-dihydroxy-phenyl; and
R is

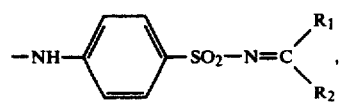

(IIa)

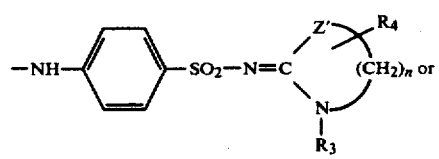

(IIb)

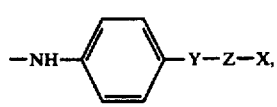

where
$R_1$ and $R_2$, which may be identical to or different from each other, are each methylmercapto or amino;
Z' is oxygen, sulfur or =NR$_3$;
$R_3$ is hydrogen, alkyl of 1 to 3 carbon atoms or hydroxy-(alkyl of 1 to 3 carbon atoms);
$R_4$ is hydrogen, hydroxyl, hydroxymethyl or methyl;
n is 2, 3 or 4;
Y is —SO$_2$NH—, —SO— or —SO$_2$—;
Z is straight or branched alkylene of 1 to 3 carbon atoms;
X is hydroxyl, aminocarbonyl, aminosulfonyl, formylamino, acetylamino, amino, methylsulfinyl, methylsulfonyl or

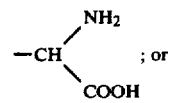

; or

—Y—Z—X is

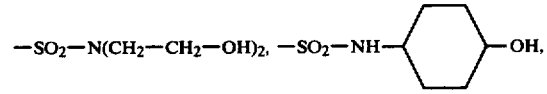

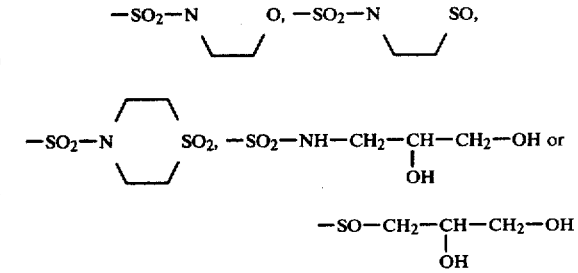

and non-toxic, pharmacologically acceptable salts thereof formed with inorganic or organic bases.

When one or both of $R_1$ and $R_2$ are amino, or when $R_3$ is hydrogen, the substituents of the formulas IIa and IIb may also occur in their tautomeric forms

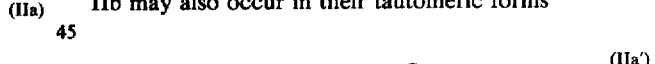 (IIa')

and

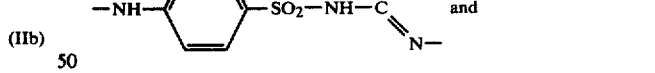 (IIb')

respectively.

A preferred subgenus is constituted by those compounds of the tautomeric formulas I and I' wherein
A is phenyl or p-hydroxy-phenyl; and
R is

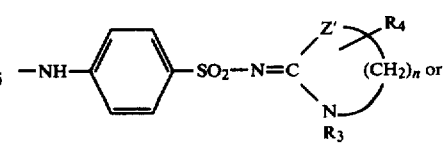

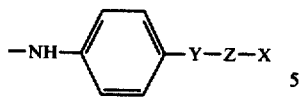  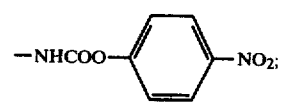

where
n is 2, 3 or 4;
Z' is =NR₃;
R₃ and R₄ are each hydrogen or methyl;
Y and Z have the meanings previously defined;
X is hydroxyl, aminocarbonyl, aminosulfonyl, acetylamino, methylsulfinyl or methylsulfonyl;
or
—Y—Z—X is

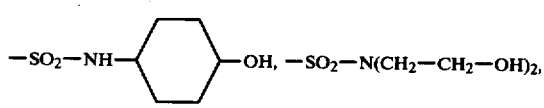

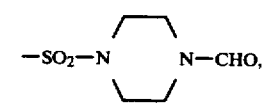

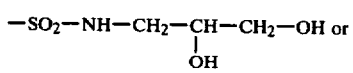

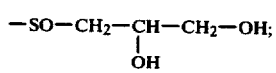

and non-toxic, pharmacologically acceptable salts thereof formed with inorganic or organic bases.

The compounds of the formulas I and I' may occur in the two possible $R_*$ and S-configurations with respect to the chiral center $\overset{*}{C}$, or also as a mixture of these two configurations. Compounds having the D=R-configuration are preferred.

The compounds of the present invention may be prepared by the following methods:

METHOD A

By reacting a compound of the formula

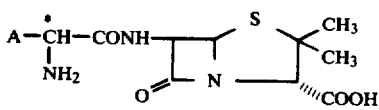

wherein A has the same meanings as in formulas I and I', with a pyrimidine derivative of the formula

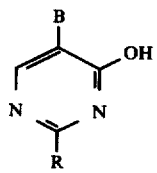

wherein
R has the same meanings as in formulas I and I', and
B is —NCO or a reactive derivative of the —NH-COOH radical, such as NHCOCl, —NHCOBr or the radical —NHCOCl is particularly preferred.

It is also possible to use mixtures of different compounds of the formula IV, where B has partly one of the above meanings and partly another, for example —NCO and —NHOCCl.

The starting compounds of the formula III may be used in the form of an inorganic or organic salt thereof, for instance as the triethylammonium salt or the sodium salt. The reaction may then be carried out in any desired mixture of water and water-miscible organic solvents such as ketones, for example acetone; cyclic ethers such as tetrahydrofuran or dioxane; nitriles such as acetonitrile; formamides such as dimethylformamide; dimethylsulfoxide; alcohols such as isopropanol; or hexametapol. The pH of the reaction mixture is maintained in the range of about 2.0 to 9.0, preferably between 6.5 and 8.0, by the addition of a base or by the use of a buffer solution.

It is, however, also possible to perform the reaction in an anhydrous solvent, for example in a halogenated hydrocarbon such as chloroform or methylene chloride, in the presence of a base, preferably triethylamine, diethylamine or N-ethyl-piperidine.

The reaction may further be carried out in a mixture of water and a water-immiscible solvent such as ethers, for example diethyl ether; halogenated hydrocarbons such as chloroform or methylene chloride; carbon disulfide; ketones such as isobutyl methyl ketone; esters such as ethyl acetate; or aromatic solvents such as benzene, advantageously accompanied by vigorous stirring, while maintaining the pH of the reaction mixture within the range of about 2.0 to 9.0, preferably between 6.5 and 8.0, by adding a base or using a buffer solution.

The reaction may, however, also be carried out in water as the only solvent in the presence of an inorganic or organic base, or by adding a buffer.

If the starting compound for this method is a silyl derivative of a compound of the formula III, for example a mono- di- or trimethylsilyl derivative, the reaction with a compound of the formula IV is advantageously carried out in an anhydrous solvent free from hydroxyl groups, for instance in a halogenated hydrocarbon such as methylene chloride or chloroform, benzene, tetrahydrofuran, acetone, dimethylformamide or the like. The addition of a base is not essential but may be of advantage in certain cases to improve the yield and purity of the end product. Examples of bases which may optionally be added to the reaction mixture are tertiary aliphatic amines such as triethylamine, aromatic amines such as pyridine, or secondary amines which are difficult to acylate because of steric-hindrance, such as dicyclohexylamine.

Instead of a silyl ester it is also possible to use other carboxyl derivatives of α-aminobenzyl-penicillins which are conventionally employed in the preparation of semi-synthetic penicillins, such as trityl, p-nitro-benzyl or phenacyl esters. After completion of the reaction these derivatives can be converted into the penicillins of the present invention by conventional methods.

The amount of base to be added is determined, for example, by the need to maintain a specific pH value. If measurement or adjustment of the pH is not effected or is not possible or practical because of a lack of sufficient water in the solvent medium, 1.0 to 2.0 mol-equivalents of base are preferably added when non-silylated compounds of the formula III are used. When silylated compounds are used, up to one mol-equivalent of base is added.

In principle, any inorganic or organic base conventionally used in organic synthesis may be employed, such as alkali metal hydroxides; alkaline earth metal hydroxides; alkaline earth metal oxides; alkali metal carbonates and bicarbonates; alkaline earth metal carbonates and bicarbonates; ammonia; primary, secondary or tertiary aliphatic amines; aromatic amines; or heterocyclic amines. Specific examples are sodium hydroxide, potassium hydroxide, calcium hydroxide, calcium oxide, sodium carbonate, potassium carbonate, sodium bicarbonate, potassium bicarbonate, ethylamine, N-methyl-ethylamine, triethylamine, hydroxyethyl-amine, aniline, pyridine or piperidine. However, when silylated starting compounds are used, the above restrictions regarding the type of base should be observed.

The buffer system may be any conventional buffer mixture, such as phosphate buffers, citrate buffers or tris(hydroxymethyl)amino-methane buffers.

The reaction temperature may vary within a fairly wide range. Generally, the reaction is carried out between about −20° and +50° C., preferably between 0° and +20° C.

The reactants of the formulas III and IV are generally caused to react with each other in equimolar amounts. However, in some cases it is advantageous to provide one of the reactants in excess in order to aid in the purification of the end product or increase the yield.

METHOD B

By reacting a ureidocarboxylic acid of the formula

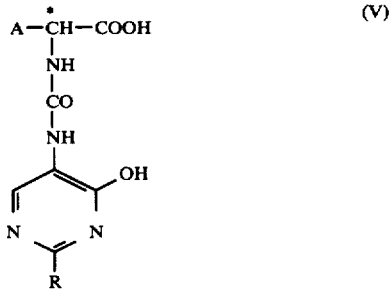

(V)

wherein A and R have the same meanings as in formulas I and I', or a salt or a reactive derivative thereof, with 6-amino-penicillanic acid of the formula

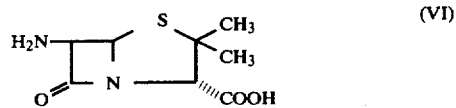

(VI)

or with an inorganic or organic salt or a derivative thereof which can be easily converted into 6-amino-penicillanic acid. The reaction product formed thereby may subsequently be converted into a penicillin of the formula I or I' by hydrolysis or catalytic hydrogenation.

Examples of suitable reactive derivatives of the ureidocarboxylic acids of the formula V are the acid anhydrides thereof such as those derived from esters of chloroformic acid, for instance ethyl or isobutyl chloroformate; or reactive esters thereof, such as the p-nitrophenyl ester or the N-hydroxysuccinimide ester; or reactive amides thereof, such as N-carbonylimidazole; but also acid halides thereof, such as the corresponding acid chloride or the acid azides. In principle, however, all the linking methods known in β-lactam chemistry may be used.

The 6-amino-penicillanic acid is advantageously used in the form of one of its derivatives. Suitable derivatives include, for example, the trimethylsilyl ester, trityl ester, p-nitrobenzyl ester, phenacyl ester and the O,N-bis-trimethylsilyl derivative. These derivatives are preferably reacted in an aprotic solvent such as methylene chloride or tetrahydrofuran. However, the 6-amino-penicillanic acid may also be used in the form of its salts, for instance its triethylammonium salt; then, for example, methylene chloride or a protic solvent or an aqueous medium or an aqueous-organic solvent, such as tetrahydrofuran/water mixtures, are used.

The ureidocarboxylic acid, its salts or its reactive derivatives are reacted with the 6-amino-penicillanic acid or its derivatives in a solvent at temperatures between −40° and +40° C., optionally in the presence of a base. If, for example, an anhydride of the ureidocarboxylic acid, such as the anhydride with ethyl chloroformate, is reacted with a derivative of 6-amino-penicillanic acid, the reaction is carried out with cooling, for example at −10° to +10° C., in a solvent such as acetone, tetrahydrofuran, dimethylformamide, chloroform, dichloromethane, hexametapol or in a mixture of two or more of these solvents. If, for example, an N-hydroxysuccinimide ester of the ureidocarboxylic acid is reacted with the 6-amino-penicillanic acid, the reaction is preferably carried out at 0° to 20° C. in the presence of a base such as triethylamine, in a solvent such as dimethylformamide, dichloromethane, dioxane or in a mixture of two or more of such solvents.

The reaction of a ureidocarboxylic acid of the formula IV itself or of a salt thereof with 6-amino-penicillanic acid or a salt thereof is advantageously carried out in the presence of a condensing agent, for instance in the presence of N,N'-dicyclohexyl-carbodiimide.

If a derivative of 6-amino-penicillanic acid is used, such as one of the above-mentioned esters thereof, it is possible, depending on the reaction conditions, that a reaction product which still contains the ester function, for example, is obtained. However, a reaction product of this kind can readily be converted into a penicillin of the formula I. If, for example, the carboxyl group of the 6-amino-penicillanic acid is present in the form of its silyl ester, after reaction it may also be present in the resulting penicillin of the formula I in the form of its silyl ester. In this case, after the actual reaction, this silyl ester group is removed by hydrolysis, so that the penicillin of the formula I or I' is obtained.

After the reaction is complete, the reaction mixture obtained by method A or B is worked up using the methods conventionally used for β-lactam antibiotics; the same applies to the isolation and purification of the end products, such as the liberation of the acid from its salts and the conversion of the free acid into other salts by means of inorganic or organic bases. For the preparation of the potassium or sodium salts, it has proved particularly advantageous to precipitate these salts from an alcoholic-ethereal solution of the free acid, by adding potassium or sodium 2-ethyl-hexanoate.

The compounds of the formula III used as starting compounds are known from the literature, cf., for example, E. H. Flynn, *Cephalosporins and Penicillins*, Academic Press, New York and London (1972).

The starting compounds of the formula IV may be obtained, for example, by reacting a corresponding 5-aminopyrimidine of the formula

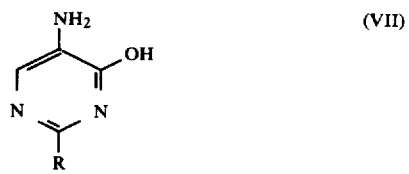

(VII)

wherein R has the meanings previously defined, with phosgene. This reaction is preferably carried out in a solvent which does not contain hydroxyl groups, such as tetrahydrofuran, methylene chloride, chloroform, dimethoxy-ethane or hexametapol, at temperatures of between −40° and +60° C., preferably between −10° and +20° C. It is advisable to bind the resulting hydrogen chloride with an equimolar amount of an inert organic base such as triethylamine or pyridine. Pyridine in excess may also be used as the solvent. If the respective aminopyrimidine of the formula VII does not dissolve readily in one of the above-mentioned solvents, phosgenation may also be effected in the heterogeneous phase. Moreover, in a particularly preferred embodiment, an aminopyrimidine of the formula VII may be converted, by treating it with a silylating agent such as hexamethyldisilazane, trimethylchlorosilane/triethylamine or trimethylsilyl-diethylamine, into an aminopyrimidine which is generally very readily soluble in the above-mentioned solvents and which is mono- or polysilylated, depending on the exchangeable hydrogen atoms present, and which then reacts with phosgene to form the corresponding compound of the formula VI. Depending on the type of solvent, the temperature, the quantity and the nature of the base which is used, either the corresponding isocyanate or carbamic acid halide is predominantly formed, or a mixture of these two compounds is formed. Depending on the reaction conditions, the compound of the formula IV is also partly or wholly present as a dihydro-oxazolopyrimidine of the formula

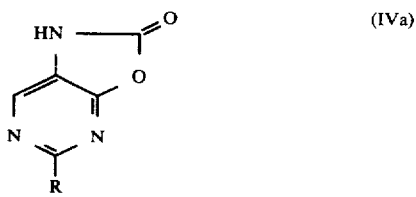

(IVa)

which is isomeric with respect to the isocyanate.

The starting compounds of the formula IV obtained by phosgenation or the mixtures thereof are generally readily soluble in the above-mentioned solvents and, after removal of the excess phosgene, can be reacted directly, without further purification, with the corresponding penicillin derivative of the formula III.

The 5-amino-4-hydroxy-2-substituted pyrimidines of the formula VII may be prepared by the following method, for example:

By reacting the 2-chloro- or 2-methylmercapto-4-hydroxy-5-nitropyrimidine of the formula VIII below [cf. Vorbrüggen and Strehlke, Chem. Ber. 106, Page 3039 (1973)] with a substituted aniline of the formula IX of IX', and subsequently reducing the nitro group of the resulting compound of the formula X, wherein R has the meanings previously defined, by known methods, in accordance with the following reaction scheme:

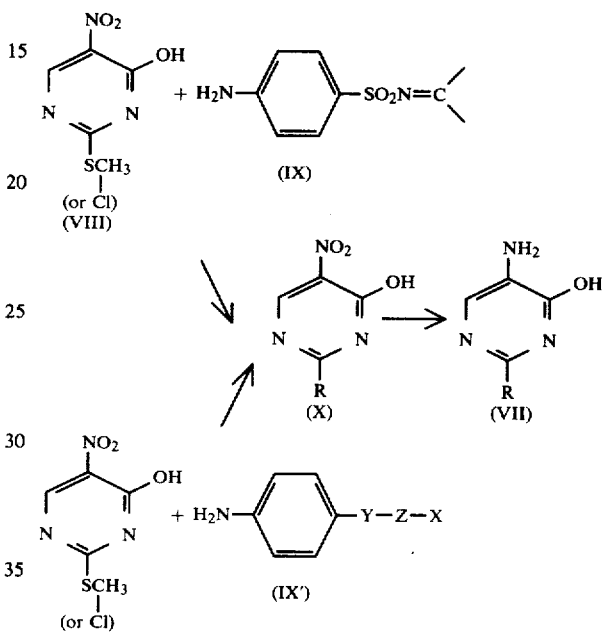

Examples of the preparation of the substituted anilines of the formula IX and of the pyrimidines X and VII are given in Examples A to E below.

The ureidocarboxylic acids of the formula V can be obtained by reacting a pyrimidine derivative of the formula IV with a glycine derivative of the formula

(XI)

wherein A has the meanings previously defined. The reaction is carried out at temperatures between −20° and +40° C., preferably between 0° C. and +20° C., in a solvent. Suitable solvents include, for example, mixtures of water and water-miscible organic solvents such as acetone, tetrahydrofuran, dioxane, acetonitrile, dimethylformamide, ethanol and dimethylsulfoxide. It may be necessary to use a hydrogen halide-binding agent; suitable hydrogen halide-binding agents are, for example, trialkylamines, such as triethylamine, or inorganic bases such as dilute sodium hydroxide.

The following examples illustrate the present invention and will enable others skilled in the art to understand it more completely. It should be understood, however, that the invention is not limited solely to the particular examples given below.

Preparation of the starting compounds:

EXAMPLE A

5-Amino-4-hydroxy-2-[p-(3',4',5',6'-tetrahydro-pyrimidin-2'-yl)-aminosulfonylanilino]-pyrimidine 27.6 gm (0.1 mol) of 4-(bismethylthio-methyleneimino)sulfonyl-aniline (C.A. 63, 8343b, 1965) and 9.2 gm (0.1 mol) of 1,3-diaminopropane were boiled for 3 hours in 200 ml of anhydrous ethanol. The precipitate formed thereby was suction-filtered off while hot. 17.5 gm (69% of theory) of p-(3',4',5',6'-tetrahydro-pyrimidin-2'-yl)-aminosulfonylaniline, m.p. 223°–225° C. were obtained.

3.4 gm (13.4 mmols) of this compound were heated to 90° C. in 80 ml of water, and 3.5 gm (17.7 mmols) of sodium 2-chloro-4-hydroxy-5-nitro-pyrimidine were added in portions. After one hour of stirring at 90° C., the mixture was cooled and suction-filtered. 3.2 gm (60% of theory) of 2-[p-(3',4',5',6'-tetrahydro-pyrimidine-2'-yl)-aminosulfonylanilino]-4-hydroxy-5-nitro-pyrimidine, m.p. >270° C., were obtained.

4 gm (11 mmols) of this product were dissolved in a mixture of 50 ml of concentrated aqueous ammonia and 100 ml of water. After the addition of 8.9 gm (51 mmols) of sodium dithionite, the mixture was stirred for one hour at room temperature. Acetic acid was then added, while cooling with ice, to give a pH of 6.9 to 7.0, and the product precipitated thereby was washed with a little ice-cold water and dried. 3.1 gm (85% of theory) of the title compound were obtained, which decomposed beginning at 250° C.

Sometimes, the product was obtained not as a crystalline substance but as an oil. In that case, the oil was separated by decanting, then washed with ice-cold water, stirred with ethanol, suction-filtered and washed with ether.

NMR-Spectrum (DMSO+CD$_3$OD) Signals at ppm (80 Mhz): 1.8 (m, 2H), 3.25 (m, 4H), 7.2 (s, 1H), 7.7 (s, 4H).

The compounds of the formula

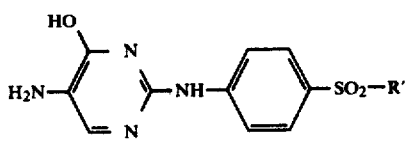

listed in the following table were prepared in analogous manner:

| R' | | NMR-Spectrum (DMSO + CD$_3$OD) signals at ppm (80 MHZ) |
|---|---|---|
| (a) | —NH–C(=O)(morpholino) | 3.6 (m, 2H), 4.4 (m, 2H), 7.1 (s, 1H), 7.65 (s, 4H). |
| (b) | —NH–C(=S)(thiazolidinyl) | 3.3–3.8 (m, 4H), 7.25 (s, 1H), 7.8 (s, 4H). |
| (c) | —NH–C(=N)(NH imidazolinyl) | 3.6 (t, 4H), 7.1 (s, 1H), 7.65 (s, 4H). |
| (d) | —NH–C(=N)(N–CH$_3$ imidazolinyl) | 2.8 (s, 3H), 3.5 (s, 4H), 7.25 (s, 1H), 7.7 (s, 4H) |
| (e) | —N(CH$_3$)–C(=N–CH$_3$) (imidazolinyl) | 2.95 (s, 6H), 3.6 (s, 4H), 7.2 (s, 1H), 7.7 (s, 4H). |
| (f) | —N=C(O)(N–CH$_3$ oxazolidinyl) | 2.9 (s, 3H), 3.7 (m, 2H), 4.5 (m, 2H), 7.2 (s, 1H), 7.7 (s, 4H). |
| (g) | —NH–C(=N)(NH, OH-tetrahydropyrimidinyl) | 3.2 (m, 4H), 7.2 (s, 1H), 7.65 (s, 4H). |
| (h) | —N(H)–C(=N)(O, CH$_2$OH oxazolinyl) | 3.6 (m, 4H), 4.7 (m, 1H), 7.2 (s, 1H), 7.75 (s, 4H). |
| (i) | —N=C(NH$_2$)$_2$ | 7.1 (s, 1H), 7.65 (s, 4H). |
| (j) | —N=C(SCH$_3$)(NH$_2$) | 2.25 (s, 3H), 7.1 (s, 1H), 7.7 (s, 4H). |
| (k) | —NH–C(=N)(NH, CH$_3$-tetrahydropyrimidinyl) | 1.2 (d, 3H), 3.1 (m, 1H), 3.5–3.9 (m, 2H), 7.15 (s, 1H), 7.7 (s, 4H). |
| (l) | —NH–C(tetrahydropyrimidinyl) | 1.5 (s broad, 4H), 3.1 (s broad, 4H), 7.15 (l, 1H), 7.65 (s, 4H). |

| R' | | NMR-Spectrum (DMSO + CD₃OD) signals at ppm (80 MHZ) |
|---|---|---|
| (m) | 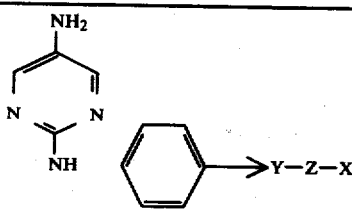 | 1.8 (m, 2H), 2.9 (s, 3H), 3.2 (m, 4H), 7.15 (s, 1H), 7.65 (s, 4H). |
| (n) | 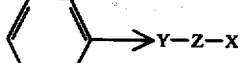 | 3.1–3.5 (m + s broad, 8H), 7.1 (s, 1H), 7.6 (s, 4H). |

EXAMPLE B

5-Amino-4-hydroxy-2-p-(2'-hydroxyethyl)-aminosulfonylanilino-pyrimidine 22.1 gm of p-nitrobenzene sulfonic acid chloride were dissolved in 100 ml of acetone and, while cooling with ice, a solution of 12.5 gm of aminoethanol in water was added. The mixture was allowed to stand for two hours at room temperature, and then the solid precipitate was suction-filtered off.

Yield: 17.9 gm (73%) of p-nitrobenzene-(2'-hydroxyethyl)-sulfonamide.

This product was suspended in 300 ml of methanol and hydrogenated with 4 gm of Raney nickel at room temperature and normal pressure. During hydrogenation, the product dissolved.

14.4 gm of p-(2'-hydroxyethyl)-aminosulfonyl-aniline were obtained.

9.5 gm of 4-hydroxy-2-methylmercapto-5-nitro-pyrimidine and 12 gm of the aniline derivative obtained above were refluxed in 100 ml of glacial acetic acid, accompanied by stirring, while the glacial acetic acid was distilled off. The residual melt was heated at 170° C. for 15 minutes. After cooling, the solid residue was suspended in ethanol, and the suspension was stirred and then suction-filtered.

Yield: 11.1 gm (62%) of 4-hydroxy-2-(2'-hydroxyethyl)-p-sulfonylanilino-5-nitro-pyrimidine.

Alternatively, this nitro-pyrimidine may also be prepared as follows:

4.3 gm of the sodium salt of 2-chloro-4-hydroxy-5-nitro-pyrimidine monohydrate were stirred with 4.4 gm of p-(2'-hydroxyethyl)-aminosulfonylaniline for one hour in 100 ml of water at 80° C. The precipitated nitro-pyrimidine was suction-filtered off and dried.

8 gm of the nitro compound obtained in this way were suspended, together with 3 gm of 20% palladium-on-charcoal as the catalyst, in 150 ml of methanol to which 15 ml of concentrated hydrochloric acid were added. The mixture was hydrogenated at room temperature while being shaken.

The hydrogen uptake (~1.5 liters) was finished after about 50 minutes. The catalyst was removed by filtering, and the filtrate was evaporated to dryness. The colorless hydrochloride residue was dissolved in 100 ml of water, and concentrated sodium hydroxide was added, while cooling with ice, until a pH of 4.5 was obtained. The oxidation-sensitive product precipitated thereby was quickly suction-filtered off and dried. In order to remove any impurities, it was dissolved in a very little dimethylformamide and quickly chromatographed on a silicagel column (eluant: methylene chloride/methanol 3:1).

Yield: 3.8 gm (52%) of colorless aminopyrimidine.

This reduction may also be carried out as follows:

3.55 gm of nitro-pyrimidine, together with 10 ml of concentrated ammonia, were dissolved in 40 ml of water while gently heating, and 8 gm of sodium dithionite were added to the solution, while stirring. The initially yellow solution became colorless. In order to complete the reaction, the mixture was heated at about 60° C. for 15 minutes. It was then cooled and, while cooling with ice, concentrated hydrochloric acid was added to give a pH of 5.0. The precipitated product was suction-filtered off and dried. Under certain circumstances, the product may be purified by means of a silicagel column chromatography as in the preceding example.

Yield of the crude product: 1.85 gm.

NMR-Spectrum (DMSO+CD₃OD) Signals at ppm: 3.2 (m, 2H), 3.65 (m, 2H), 7.2 (s, 1H), 7.8 (s, 4H).

The aminopyrimidines shown in the following table were synthesized in analogous manner:

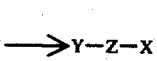

| | →Y—Z—X | NMR-Spectrum (DMSO + CD₃OD) signals at ppm: |
|---|---|---|
| (a) | —SO₂N(CH₂CH₂OH)₂ | 3.25 (m, 4H), 3.70 (m, 4H), 7.15 (s, 1H), 7.8 (s, 4H). |
| (b) | 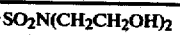 | 1.2–1.8 (m, 8H), 3.0 (m, 1H), 3.6 (m, 1H), 7.2 (s, 1H), 7.75 (s, 4H). |
| (c) |  | 2.85 (broad t, 4H), 3.6 (broad signal, 4H), 7.20 (s, 1H), 7.75 (q, 4H). |
| (d) | —SO₂NHCH₂CONH₂ | 3.55 (t, 2H), 7.3 (s, 1H), 7.7 (s, 4H). |
| (e) |  | 2.9 (m, 4H), 3.45 (m, 4H), 7.25 (s, 1H), 7.75 (q, 4H), 7.95 (s, 1H). |
| (f) | —SO₂NH(CH₂)₃CONH₂ | 1.70 (q, 2H), 2.15 (t, 2H), 2.75 (t, 2H), 7.20 (s, 1H), 7.8 (broad s, 4H). |
| (g) | —SO₂NHCH₂CH₂NHCOCH₃ | 1.8 (s, 3H), 2.8 (m, 2H), 3.2 (m, 2H), 7.2 (s, 1H), 7.7 (s, 4H). |
| (h) | —SO₂NHCH₂CH₂COOH | 2.4 (t, 2H), 2.95 (t, 2H), 7.2 (s, 1H), 7.75 (q, 4H). |

EXAMPLE C

5-Amino-4-hydroxy-2-p-(2'-hydroxyethyl)-sulfinylanilino-pyrimidine 4.1 gm (0.052 mol) of 2-mercapto-ethanol were added dropwise to a solution of 1.2 gm of sodium (0.052 mol)

in 50 ml of ethanol. To the resulting solution of the mercaptide, 7.05 gm (0.05 mol) of 4-fluoro-nitrobenzene were added dropwise, while cooling with ice. The mixture was refluxed for 10 minutes and then evaporated in vacuo. The residue was taken up in water, and the oil which separated out was extracted with ethyl acetate. After the extract solution had been dried and the ethyl acetate had been distilled off, an oil was obtained which crystallized when allowed to stand for a fairly long time.

Yield: 9.1 gm (91.4%) of 2-hydroxyethyl-p-nitrophenyl sulfide.

7.1 gm (0.035 mol) of 2-hydroxyethyl-p-nitrophenyl sulfide were dissolved in 50 ml of glacial acetic acid, 4 ml of 30% hydrogen peroxide (0.038 mol) were added, and the mixture was allowed to stand for 3 days in the refrigerator. After the solvents had been distilled off in vacuo, the residue was purified by chromatography on a silicagel column (eluant: chloroform/methanol 30:1).

Yield: 3.8 gm (48%) of 2-hydroxyethyl-p-nitrophenylsulfoxide.

3.7 gm (0.017 mol) of 2-hydroxyethyl-p-nitrophenylsulfoxide were dissolved in 200 ml of methanol and hydrogenated in the presence of 0.5 gm of Raney nickel at room temperature and 5 bars. After the catalyst had been filtered off, the filtrate was evaporated to dryness.

Yield: 3.2 gm (100%) of p-(2-hydroxyethyl)-sulfinyl-aniline.

To the solution of 3.2 gm (0.017 mol) of p-(2-hydroxyethyl)-sulfinyl-aniline, 3.7 gm (0.017 mol) of 2-chloro-4-hydroxy-5-nitropyrimidine-sodium x 1 H₂O were added.

The solution was heated on a steam bath for 30 minutes, then cooled and the precipitate formed thereby was suction-filtered off.

Melting point: 256° C. (decomp.).

Yield: 3.7 gm (65%) of 4-hydroxy-2-p-(2'-hydroxyethylsulfinyl-anilino-5-nitro-pyrimidine.

1 gm (0.003 mol) of 4-hydroxy-2-p-(2'-hydroxyethyl)-sulfinyl-anilino-5-nitro-pyrimidine was dissolved in 10 ml of concentrated ammonia and 40 ml of water, then 2.7 gm (0.015 mol) of sodium dithionite were added, and the mixture was heated on a steam bath for 30 minutes. The solution was evaporated to dryness, and the residue was extracted by boiling with methanol. The crude product was purified by chromatography on a silicagel column (eluant: chloroform/methanol 2:1).

Yield: 290 mg (32%) of 5-amino-4-hydroxy-2-p-(2'-hydroxyethyl)-sulfinyl-anilino-pyrimidine.

NMR-spectrum (DMSO+CD₃OD) signals at ppm: 2.9 (t, 2H), 3.7 (m, 2H), 7.15 (s, 1H), 7.65 (q, 4H).

The aminopyrimidines shown in the following table were synthesized in analogous manner:

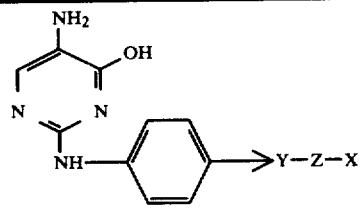

| Y—Z—X | NMR-Spectrum (DMSO + CD₃OD) Signals at ppm: |
|---|---|
| (a) —SO₂—CH₂—CH₂OH | 3.5 (d,d,4H), 7.1 (s, 1H), 7.7 (s, 4H). |
| (b) —SO₂—CH₂—CH₂—SO₂—CH₃ | 3.05 (s, 3H), 3.5 (m, 4H), 7.2 (s, 1H), 7.8 (s, 4H). |
| (c) —SO—CH(CH₃)(CH₂—OH) | 0.9 (t, 3H), 2.8 (m, 1H), 3.65 (m, 2H), 7.15 (l, 1H), 7.7 (m, 4H). |
| (d) —SO—CH₂—CH(OH)(CH₃) | 1.25 (m, 3H), 2.9 (m, 2H), 3.8 (m, 1H), 7.25 (s, 1H), 7.75 (m, 4H). |
| (e) —SO—CH₂—CH(OH)—CH₂—OH | 2.9 (m, 2H), 3.45 (d, 2H), 3.85 (m, 1H), 7.2 (s, 1H), 7.75 (q, 4H). |

EXAMPLE D

D,L-α-[3-{2-p-(2'-hydroxyethyl)-aminosulfonyl-anilino}-5-pyrimidinyl}-ureido]-thienylglycine 1.63 gm (5 mmols) of 5-amino-4-hydroxy-2-p-(2'-hydroxyethyl)-aminosulfonyl-anilino-pyrimidine were suspended in 50 ml of anhydrous tetrahydrofuran, and the suspension was stirred with 20 ml of trimethylsilyl-diethylamine until everything substantially dissolved (about 1 hour at 20° to 40° C.). Any residual insoluble matter was filtered off while moisture is excluded, and the filtrate was evaporated to dryness. The residue was taken up in 50 ml of tetrahydrofuran, and the solution was added dropwise to an ice-cooled solution of 0.5 gm (5 mmols) of phosgene in 20 ml of anhydrous tetrahydrofuran. The mixture was stirred for 15 minutes at room temperature, then evaporated to dryness, and the residue was taken up in 50 ml of tetrahydrofuran (solution I).

800 mg (5.5 mmols) of D,L-α-thienylglycine were suspended in 100 ml of 80% aqueous tetrahydrofuran, and the suspension was mixed with 5.5 ml of 1 N sodium hydroxide solution, whereupon a solution was formed. Solution I was added dropwise at 0° to 5° C., and the mixture was stirred for 30 minutes at 0° C. and at room temperature for 1 hour. Then 100 ml of water were added, and the tetrahydrofuran was evaporated in vacuo. The aqueous phase was extracted with ethyl acetate, the organic phase was discarded, and the aqueous phase was adjusted to pH 2.6 with 2 N hydrochloric acid. The precipitate formed thereby was suction-filtered off and dried. 1.45 gm (57%) of the title compound are obtained.

NMR-spectrum (DMSO+CD₃OD) signals at ppm: 3.2 (m, 2H), 3.60 (m, 2H), 5.50 (s, 1H), 7.0 (m, 2H), 7.4 (d, 1H), 7.8 (s, 4H), 8.34 (s, 1H).

The ureidocarboxylic acids shown in the following table were prepared in analogous manner:

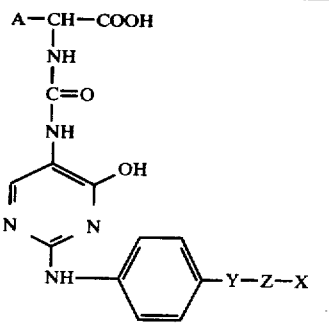

| A | −Y−Z−X | NMR-Spectrum (DMSO + CD₃OD) Signals at ppm: | Yield % |
|---|---|---|---|
| (a) furan-like structure with S | −SO₂NH(CH₂)₃CONH₂ | 1.75 (m, 2H), 2.20 (m, 2H), 2.85 (m, 2H), 5.5 (s, 1H), 7.0 (m, 2H), 7.45 (d, 1H), 7.75 (s, 4H), 8.35 (s, 1H). | 46 |
| (b) HO, HO-phenyl | −SO₂NHCH₂CH₂OH | 3.15 (m, 2H), 3.55 (m, 2H), 5.20 (s,1H), 6.7 (s,2H), 6.85 (s,1H), 7.75 (broad s, 4H), 8.30 (s, 1H). | 52.5 |
| (c) HO-phenyl | −S(O)−CH₂CH₂−OH | 2.9 (m,2H), 3.75 (m,2H), 5.15 (s,1H), 6.80 (d,2H), 7.25 (d,2H), 7.70 (q,4H), 8.32 (s,1H). | 42 |

EXAMPLE E

D-α-[3-(4-hydroxy-2-{p-(3',4',5',6'-tetrahydro-pyrimidin-2'-yl)-aminosulfonyl-anilino}-5-pyrimidinyl)-ureido]-p-hydroxy-phenylglycine 2.0 gm (5.5 mmols) of 5-amino-4-hydroxy-2-{p-(3',4',5',6'-tetrahydropyrimidin-2'-yl)-aminosulfonyl-anilino}-pyrimidine were suspended in 50 ml of anhydrous tetrahydrofuran, and the suspension was stirred with 20 ml of trimethylsilyl-diethylamine until everything substantially dissolved (about 1 hour at 20°-40° C.). The mixture was filtered to remove any remaining insoluble components, while moisture was excluded, and the filtrate was evaporated to dryness. The residue was taken up in 50 ml of tetrahydrofuran, and the solution was added dropwise to an ice-cooled solution of 0.544 gm (5 mmols) of phosgene in 20 ml of anhydrous tetrahydrofuran. The mixture was stirred at room temperature for 15 minutes, then evaporated to dryness, and the residue was taken up in 50 ml of tetrahydrofuran (solution I).

0.6 gm (3.6 mmols) of D-α-p-hydroxyphenylglycine were suspended in 100 ml of aqueous 80% tetrahydrofuran, and the suspension was mixed with 3.6 ml of 1 N sodium hydroxide, whereupon a solution was formed. At 0° to 5° C., solution I was added dropwise thereto, and the mixture was stirred for 30 minutes at 0° C. and one hour at room temperature. Then 100 ml of water were added, and the tetrahydrofuran was removed in vacuo. The aqueous phase was extracted with ethyl acetate, the organic phase was discarded, and the aqueous phase was adjusted to pH 2.6 with 2 N hydrochloric acid. The precipitate formed thereby was suction-filtered and dried. 0.9 gm (45% of theory) of the title compound were obtained, which decomposed at about 250° C.

NMR-Spectrum (DMSO+CD₃OD) signals at ppm (80 MHz): 1.75 (m, 2H), 3.2 (m, 4H), 5.15 (s, 1H), 6.8–7.25 (q, 4H), 7.75 (s, 4H), 8.3 (s, broad, 1H).

The compounds of the formula

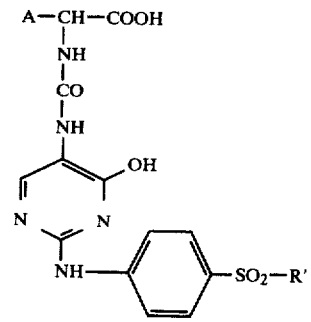

shown in the following table were prepared analogously:

| A | R' | NMR-Spectrum (DMSO + CD₃OD) Signal at ppm (80 MHz) |
|---|---|---|
| (a) HO-phenyl | −NH−C(=N)− thiazoline ring (S) | 3.3–3.7 (m, 4H), 5.15 (s, 1H), 6.8–7.25 (q, 4H), 7.75 (s, 4H), 8.3 (s, 1H). |
| (b) HO-phenyl | −NH−C(=N)− oxazoline ring (O) | 3.15 (m, 2H), 3.4 (q, 2H), 5.1 (s, 1H), 6.75–7.2 (q, 4H), 7.7 (s, 4H), 8.25 (s, broad, 1H). |

-continued

| A | R' | NMR-Spectrum (DMSO + CD₃OD) Signal at ppm (80 MHz) |
|---|----|----|
| (c) phenyl-, NH-C(=N-)-NH-CH₂CH₂CH₂- (tetrahydropyrimidinyl) | H-N | 1.75 (m, 2H), 3.25 (m, 4H), 5.10 (s, 1H), 7.40–7.80 (m, 9H), 8.25 (s, 1H). |

Preparation of end products:

EXAMPLE 1

Sodium
D-α-[3-(4-hydroxy-2-{p-(3',4',5',6'-tetrahydro-pyrimidin-2'-yl)-aminosulfonyl-anilino}-5-pyrimidinyl)-ureido]-p-hydroxybenzyl-penicillin 1.0 gm (2.75 mmols) of 5-amino-4-hydroxy-2-{p-(3',4',5',6'-tetrahydro-pyrimidin-2'-yl)-aminosulfonylanilino}-pyrimidine were suspended in 50 ml of anhydrous tetrhydrofuran, and after the addition of 5 ml of trimethylsilyl-diethylamine the mixture was stirred for 2½ hours at room temperature. The reaction mixture was then evaporated to dryness at 30° C. and dried for 30 minutes in a high vacuum. The residue was taken up in 50 ml of anhydrous tetrahydrofuran and added dropwise at 0° to 5° C. to 3.4 ml of a solution of 20 gm of phosgene in 250 ml of anhydrous tetrahydrofuran. The mixture was stirred for 30 minutes at room temperature and was then evaporated to dryness at a maximum temperature of 30° C. The residue was taken up in 40 ml of tetrahydrofuran (solution I).

1.1 gm (2.6 mmols) of amoxicillin trihydrate were suspended in 100 ml of aqueous 80% tetrahydrofuran and caused to dissolve by adjusting the pH value to 8.3 (triethylamine). Solution I was added dropwise at 5° to 10° C., and the pH was maintained at 7.5 by the addition of triethylamine. The mixture was stirred for 1 hour at room temperature, then 100 ml of water were added, and the tetrahydrofuran was removed in vacuo at 30° C. The residual aqueous solution was adjusted to pH 2.3 with 2 N hydrochloric acid while cooling, and the precipitate formed thereby was collected by centrifuging, washed with water and dried (1.6 gm). The product was suspended in methanol, and 0.55 gm (3.3 mmols) of sodium 2-ethylhexanoate were added to the suspension. After the addition of diethyl ether, 1.3 gm (62.5% of theory) of the title compound were obtained as a colorless powder.

NMR-spectrum (DMSO+CD₃OD) signals at ppm (80 MHz): 1.4–1.8 (d+m, 8H), 3.2 (s,broad,4H), 4.05 (s, 1H), 5.4 (m, 3H), 6.75/7.25 (q, 4H), 7.75 (q, 4H), 8.3 (s, 1H).

IR-spectrum: 1765 cm⁻¹.

The compounds of the formula

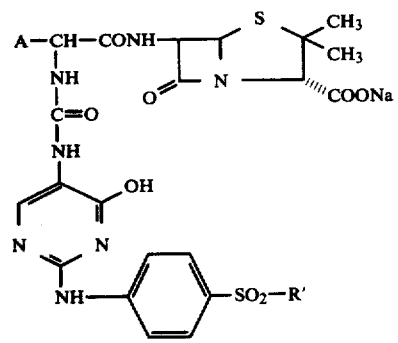

listed in the following table were prepared analogously:

| Example No. | A | R' | IR-Spectrum cm⁻¹ | NMR-Spectrum (DMSO + CD₃OD) signals at ppm (80 MHz). |
|---|---|---|---|---|
| 2 | HO-C₆H₄- | -NH-C(=O)-(morpholinyl, O) | 1760 | 1.5 (d, 6H), 3.6 (m, 2H), 4.05 (s, 1H), 4.4 (m, 2H), 5.4 (m, 3H), 6.7/7.2 (q, 4H), 7.75 (q, 4H), 8.3 (s, 1H). |
| 3 | HO-C₆H₄- | -NH-C(=S)-(thiazinyl) | 1765 | 1.55 (d, 6H), 3.3–3.7 (m, 4H), 4.05 (s, 1H), 5.45 (m, 3H), 6.75/7.25 (q, 4H), 7.8 (q, 4H), 8.3 (s, 1H). |
| 4 | HO-C₆H₄- | -NH-C(=N-H)-(tetrahydropyrimidinyl) | 1765 | 1.5 (d, 6H), 3.45 (s, 4H), 4.05 (s, 1H), 5.4 (m, 3H), 6.75/7.2 (q, 4H), 7.7 (s, 4H), 8.3 (s, 1H). |
| 5 | HO-C₆H₄- | -NH-C(=N-CH₃)-(tetrahydropyrimidinyl) | 1760 | 1.55 (d, 6H), 2.8 (s, 3H), 3.5 (s, 4H), 4.05 (s, 1H), 5.5 (m, 3H), 6.8/7.3 (q, 4H), 7.8 (q, 4H), 8.35 (s, 1H). |

-continued

| Example No. | A | R' | IR-Spectrum cm$^{-1}$ | NMR-Spectrum (DMSO + CD$_3$OD) signals at ppm (80 MHz). |
|---|---|---|---|---|
| 6 | HO—C$_6$H$_4$— | —N=C(N(CH$_3$)CH$_2$CH$_2$CH$_2$N(CH$_3$)) (1,3-dimethyl-tetrahydropyrimidin-2-ylidene) | 1765 | 1.5 (d, 6H), 2.9 (s, 6H), 3.5 (s, 4H), 4.0 (s, 1H), 5.45 (m, 3H), 6.675/7.25 (q, 4H), 7.75 (m, 4H), 8.25 (s, 1H). |
| 7 | HO—C$_6$H$_4$— | —N=C(O-CH$_2$CH$_2$-N(CH$_3$)) | 1765 | 1.55 (d, 6H), 2.85 (s, 3H), 3.6 (m, 2H), 4.1 (s, 1H), 4.5 (m, 2H), 5.4 (m, 3H), 6.75/7.25 (q, 4H), 7.75 (q, 4H), 8.3 (s, 1H). |
| 8 | HO—C$_6$H$_4$— | —NH—C(=N—)(NH—) cyclic (tetrahydropyrimidin-2-yl-amino) | 1760 | 1.55 (d, 6H), 3.3 (m, 4H), 4.05 (s, 1H), 5.4 (m, 3H), 6.7/7.25 (q, 4H), 7.75 (q, 4H), 8.25 (s, 1H). |
| 9 | HO—C$_6$H$_4$— | —NH—C(=N—CH$_2$—CH(CH$_2$OH)—O—) | 1765 | 1.5 (d, 6H), 3.6 (m, 4H), 4.05 (s, 1H), 4.8 (m, 1H), 5.5 (m, 3H), 6.8/7.25 (q, 4H), 7.8 (q, 4H), 8.3 (s, 1H). |
| 10 | HO—C$_6$H$_4$— | —N=C(NH$_2$)(NH$_2$) | 1770 | 1.5 (d, 6H), 4.05 (s, 1H), 5.4 (m, 3H), 6.75/7.2 (m, 4H), 7.75 (m, 4H), 8.3 (s, 1H). |
| 11 | HO—C$_6$H$_4$— | —N=C(SCH$_3$)(NH$_2$) | 1760 | 1.55 (d, 6H), 2.25 (s, 3H), 4.0 (s, 1H), 5.4 (m, 3H), 6.7/7.25 (q, 4H), 7.75 (q, 4H), 8.3 (s, 1H). |
| 12 | C$_6$H$_5$— | —NH—C(=N—)(NH—) cyclic (tetrahydropyrimidin-2-yl-amino) | 1765 | 1.45–1.8 (d + m, 8H), 3.2 (m, 4H), 4.05 (s, 1H), 5.45 (m, 3H), 7.40–7.80 (m, 9H), 8.3 (s, 1H). |
| 13 | HO—C$_6$H$_4$— | —NH—C(=N—CH(CH$_3$)—CH$_2$—NH—) | 1770 | 1.15 (d, 3H), 1.55 (d, 6H), 3.0–3.9 (m, 3H), 4.05 (s, 1H), 5.4 (m, 3H), 6.7 (d, 2H), 7.2 (d, 2H), 7.7 (q, 4H), 8.25 (s, 1H). |
| 14 | HO—C$_6$H$_4$— | —NH—C(=N—(CH$_2$)$_4$—NH—) (hexahydrodiazepin-2-yl-amino) | 1770 | 1.1–1.7 (m, 10H), 3.15 (m, 4H), 4.05 (s, 1H), 5.4 (m, 3H), 6.7 (d, 2H), 7.2 (d, 2H), 7.7 (q, 4H), 8.2 (s, 1H). |
| 15 | HO—C$_6$H$_4$— | —NH—C(=N—(CH$_2$)$_3$—N(CH$_3$)—) | 1775 | 1.4–1.9 (d + m, 8H), 2.9 (s, 3H), 3.2 (m, 4H), 4.0 (s, 1H), 5.4 (m, 3H), 6.65 (d, 2H), 7.2 (d, 2H), 7.65 (q, 4H), 8.2 (s, 1H). |

| Example No. | A | R' | IR-Spectrum cm$^{-1}$ | NMR-Spectrum (DMSO + CD$_3$OD) signals at ppm (80 MHz). |
|---|---|---|---|---|
| 16 | HO—⟨⟩— | —NH—C(=N-CH₂CH₂OH)—N (imidazoline ring) | 1770 | 1.55 (d, 6H), 3.2-3.7 (m, 8H), 5.4 (m, 3H), 6.7 (d, 2H), 7.2 (d, 2H), 7.7 (s broad, 4H) 8.25 (s, 1H). |

EXAMPLE 17

Sodium
D-α-[3-(4-hydroxy-2-p-(2'-hydroxyethyl)-aminosulfonyl-anilino-5-pyrimidinyl)-ureido]-p-hydroxybenzyl-penicillin 980 mg (3 mmols) of 5-amino-4-hydroxy-2-p-(2'-hydroxyethyl)-aminosulfonyl-anilino-pyrimidine were suspended in 50 ml of anhydrous tetrahydrofuran, and after addition of 5 ml of trimethylsilyl-diethylamine the mixture was stirred for 2½ hours at room temperature. It was then evaporated to dryness at 30° C., and dried for 30 minutes in a high vacuum. The residue was taken up in 50 ml of anhydrous tetrahydrofuran, and at 0° to 5° C. the solution was added dropwise to 3.75 ml of a solution of 20 gm of phosgene in 250 ml of anhydrous tetrahydrofuran. The mixture was stirred for 30 minutes at room temperature and then evaporated to dryness at a maximum temperature of 30° C. The residue was taken up in 40 ml of tetrahydrofuran (solution I).

1.3 gm (3.1 mmols) of amoxycillin trihydrate were suspended in 100 ml of aqueous 80% tetrahydrofuran and dissolved therein by adjusting the pH to 8.3 (triethylamine). At 5° to 10° C., solution I was added dropwise while the pH was maintained at 7.5 by the addition of triethylamine. The mixture was stirred for one hour at room temperature, 100 ml of water were then added, and the tetrahydrofuran was removed in vacuo at 30° C. The residual aqueous solution was adjusted to pH 2.7 with 2 N hydrochloric acid while cooling, and the precipitate formed thereby was suction-filtered off, washed with water and dried (1.6 gm).

The product was suspended in methanol, and 0.55 gm (3.3 mmols) of sodium 2-ethylhexanoate was added. After the addition of diethyl ether, 1.3 gm (59% of theory) of the title compound were obtained as a colorless powder.

NMR-spectrum (DMSO+CD$_3$OD) signals at ppm: 1.55 (d, 6H), 3.2 (m, 2H), 3.55 (m, 2H), 4.0 (s, 1H), 5.40 (q, 2H), 5.45 (s, 1H), 6.70 (d, 2H), 7.25 (d, 2H), 7.80 (q, 4H), 8.35 (s, 1H).

IR-spectrum: 1765, 1660, 1610, 1155 cm$^{-1}$.

The compounds of formula

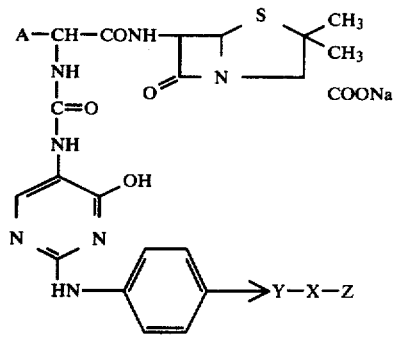

listed in the following table were prepared analogously:

| Example No. | A | —Y—Z—X | IR-Spectrum cm$^{-1}$ | NMR-Spectrum (DMSO + CD$_3$OD) signals at ppm |
|---|---|---|---|---|
| 18 | HO—⟨⟩— | —SO₂N(CH₂CH₂OH)₂ | 1765 1655 1150 | 1.55 (d,6H), 3.20 (m,4H), 3.65 (m,4H), 3.95 (s,3H), 5.45 (q,2H + s,1H), 6.75 (d,2H), 7.25 (d,2H), 7.8 (s,4H), 8.30 (s,1H). |
| 19 | HO—⟨⟩— | —SO₂NH—⟨⟩—OH | 1760 1155 | 1.55 (d,6H), 1.2-1.9 (m,8H), 3.1 (m, broad, 1H), 3.6 (m,1H), 3.95 (s,1H), 5.40 (q,2H), 5.50 (s,1H), 6.75 (d,2H), 7.3 (d,2H), 7.75 (q,4H), 8.33 (s,1H). |
| 20 | HO—⟨⟩— | —SO₂N⟨morpholino⟩O | 1765 1660 1605 1105 | 1.55 (d,6H), 2.8 (m,4H), 3.6 (m,4H), 3.95 (s,1H), 5.40 (m,3H), 6.8 (d,2H), 7.3 (d,2H), 7.8 (s,4H), 8.32 (s,1H). |
| 21 | HO—⟨⟩— | —SO₂NHCH₂CONH₂ | 1765 1150 | 1.55 (d,6H), 3.45 (s, broad, 2H) 3.95 (s,1H), 5.45 (m,3H), 6.8 (d,2H), 7.35 (d,2H), 7.8 (s,4H), 8.3 (s,1H). |

-continued

| Example No. | A | —Y—Z—X | IR-Spectrum cm$^{-1}$ | NMR-Spectrum (DMSO + CD$_3$OD) signals at ppm |
|---|---|---|---|---|
| 22 | phenyl | —SO$_2$NHCH$_2$CONH$_2$ | 1760, 1155 | 1.55 (d,6H), 3.40 (s,2H), 4.0 (s,1H), 5.45 (m,3H), 7.35 (s, broad 5H), 7.75 (s,4H), 8.32 (s,1H). |
| 23 | HO-phenyl | —SO$_2$N(piperazine)N—CHO | 1765, 1660, 1150 | 1.55 (d,6H), 2.95 (m,4H), 3.50 (m,4H), 4.0 (s,1H), 5.40 (q,2H), 5.45 (s,1H), 6.8 (d,2H), 7.3 (d,2H), 7.8 (q,4H), 8.0 (s,1H), 8.35 (s,1H). |
| 24 | HO-phenyl | —SO$_2$NHCH$_2$CH$_2$NH—COCH$_3$ | 1765, 1660, 1610, 1150 | 1.55 (d,6H), 1.8 (s,3H), 2.8 (m,2H), 3.3 (m,2H), 4.05 (s,1H), 5.45 (q,2H), 5.50 (s,1H), 6.75 (d,2H), 7.30 (d,2H), 7.75 (q,4H), 8.33 (s,1H). |
| 25 | phenyl | —SO$_2$NHCH$_2$CH$_2$NHCOCH$_3$ | 1765, 1155 | 1.50 (d,6H), 1.85 (s,3H), 2.75 (m,2H), 3.25 (m,2H), 4.0 (s, 1H), 5.45 (m,3H), 7.40 (s, broad, 5H), 7.75 (q,4H), 8.31 (s,1H). |
| 26 | HO-phenyl | —SO$_2$NHCH$_2$CH$_2$COOH | 1765, 1610, 1155 | 1.55 (d,6H), 2.35 (t,2H), 2.90 (t,2H), 3.95 (s,1H), 5.45 (m,3H), 6.8 (d,2H), 7.3 (d,2H), 7.8 (s,4H), 8.3 (s,1H). |

EXAMPLE 27

Sodium salt of D,L-α-{3-[2-p-(2'-hydroxyethyl)-amino-sulfonyl-anilino-5-pyrimidinyl]-ureido}-2-thienyl-acetamido-penicillinic acid A solution of 1.10 gm of the ureidocarboxylic acid of Example D (2 mmols) in 50 ml of dimethylformamide was mixed with 200 mg of N-methyl-morpholine. At −15° to −20° C., 205 mg (2 mmols) of ethyl chloroformate were added, and the mixture was stirred for 10 minutes at this temperature (solution I).

A suspension of 460 mg (2.1 mmols) of 6-aminopenicillanic acid in 50 ml of methylene chloride was stirred with triethylamine until everything dissolved. The solution was added at −20° C. to solution I, and the mixture was stirred for 30 minutes at −20° C. and for 2 hours at ambient temperature.

100 ml of water were added, the pH was adjusted to 7.2, and solution was extracted with ethyl acetate. The aqueous phase was adjusted to pH 2.8 (2 N hydrochloric acid) while cooling with ice, and the precipitate formed thereby was suction-filtered off, washed with ice-cold water and dried. A methanolic suspension of this product was mixed with sodium 2-ethylhexanoate, and the sodium salt was precipitated with diethyl ether.

840 mg (54% of theory) of the title compound were obtained in the form of a colorless powder.

NMR-spectrum (DMSO+CD$_3$OD) signals at ppm: 1.55 (d,6H), 3.25 (m, 2H), 3.65 (m, 2H), 4.0 (s, 1H), 5.4 (q, 2H), 5.65 (s, 1H), 7.0 (m, 2H), 7.4 (d, 1H), 8.32 (s, 1H).

IR-spectrum: 1765 cm$^{-1}$.

The compounds of the formula

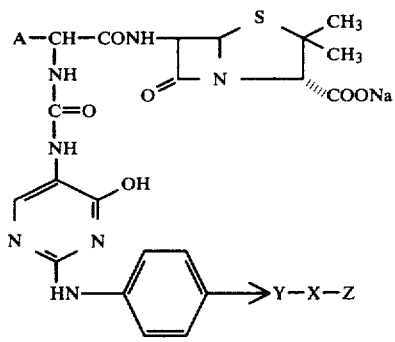

listed in the following table were prepared analogously:

| Example No. | A | Y—X—Z | IR-Spectrum cm$^{-1}$ | NMR-Spectrum (DMSO + CD$_3$OD) signals at ppm |
|---|---|---|---|---|
| 28 | thienyl | —SO$_2$NH(CH$_2$)$_3$CONH$_2$ | 1765, 1150 | 1.55 (d,6H), 1.80 (m,2H), 2.3 (m,2H), 2.85 (m,2H), 4.05 (s,1H), 5.45 (q,2H), 5.70 (s, broad, 1H), 7.0 (m,2H), 7.4 (d,1H), 7.80 (q,4H), 8.32 (s,1H). |

| Example No. | A | Y—X—Z | IR-Spectrum cm$^{-1}$ | NMR-Spectrum (DMSO + CD$_3$OD) signals at ppm |
|---|---|---|---|---|
| 29 | HO—⟨⟩—, HO— | —SO$_2$NHCH$_2$CH$_2$OH | 1765 1155 | 1.55 (d,6H), 3.20 (m,2H), 3.55 (m,2H), 5.45 (m,3H), 6.7 (s,2H), 6.85 (s,1H), 7.75 (q,4H), 8.33 (s,1H). |

EXAMPLE 30

Sodium D-α-[3-(4-hydroxy-2-{p-(3',4',5',6'-tetrahydro-pyrimidin-2'-yl)-aminosulfonyl-anilino}-5-pyrimidinyl)-ureido]-p-hydroxybenzyl-penicillin 1.8 gm (3.2 mmols) of D-α-[3-(4-hydroxy-2-{p-(3',4',5',6'-tetrahydropyrimidin-2'-yl)-aminosulfonylanilino}-5-pyrimidinyl)-ureido]-p-hydroxyphenylglycine in 80 ml of dimethylformamide were mixed with 323 mg of N-methyl-morpholine. At −15° to −20° C., 345 mg (3.2 mmols) of ethyl chloroformate were added, and the mixture was stirred for 30 minutes at this temperature (solution I).

A suspension of 690 mg (3.2 mmols) of 6-aminopenicillanic acid in 50 ml of methylene chloride was stirred with 2 gm (20 mmols) of triethylamine until a solution was formed. This solution was added at −20° C. to solution I, and the mixture was stirred for 30 minutes at −20° C. and for 2 hours at ambient temperature.

200 ml of water were added, the pH was adjusted to 7.2, and the mixture was extracted with ethyl acetate. The aqueous phase was adjusted to pH 2.3 (2 N hydrochloric acid) while cooling with ice, and the precipitate formed thereby was collected by centrifuging, washed with ice-cold water and dried. A methanolic suspension of this product was mixed with sodium 2-ethylhexanoate, and the sodium salt was precipitated with diethyl ether. 1.7 gm (68% of theory) of the title compound were obtained in the form of a colorless powder.

NMR-spectrum (DMSO+CD$_3$OD) signals at ppm (80 MHz): 1.4–1.8 (d+m, 8H), 3.25 (m, 4H), 4.05 (s, 1H), 5.4 (m, 3H), 6.70/7.2 (q, 4H), 7.8 (q, 4H), 8.3 (s, 1H). IR-spectrum: 1765 cm$^{-1}$.

The compounds of the formula

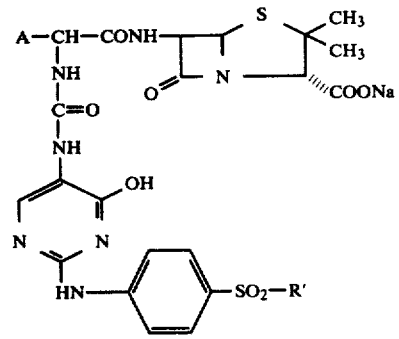

listed in the following table were prepared analogously:

| Example No. | A | R' | IR-Spectrum cm$^{-1}$ | NMR-Spectrum (DMSO + CD$_3$OD) signals at ppm (80 MHz): |
|---|---|---|---|---|
| 31 | HO—⟨⟩— | —NH—⟨S,N⟩ | 1765 | 1.50 (d,6H), 3.25–3.7 (m,4H), 4.05 (s,1H), 5.4 (m,3H), 6.75/7.2 (q,4H), 7.75 (q,4H), 8.3 (s,1H). |
| 32 | HO—⟨⟩— | —NH—⟨O,N⟩ | 1760 | 1.50 (d,6H), 3.55 (m,2H), 4.05 (s,1H), 4.4 (m,2H), 5.45 (m,3H), 6.75/7.25 (q,4H), 7.8 (q,4H), 8.3 (s,1H). |
| 33 | ⟨⟩— | —NH—⟨H-N,N⟩ | 1765 | 1.4–1.8 (d + m, 8H), 3.2 (m,4H), 4.05 (s,1H), 5.4 (m,3H), 7.40–7.80 (m,9H), 8.3 (s,1H). |

EXAMPLE 34

Sodium D-α-{3-[4-hydroxy-2-p-(2'-hydroxyethyl)-sulfinyl-anilino-5-pyrimidinyl]-ureido}-p-hydroxybenzyl-penicillin 260 mg (0.88 mmols) of 5-aminio-4-hydroxy-2-p-(2'-hydroxyethyl)-sulfinyl-anilino-pyrimidine were suspended in 10 ml of anhydrous tetrahydrofuran, 2 ml of N,N-diethyltrimethylsilylamine were added, and the mixture was refluxed for 30 minutes. After a small amount of insoluble by-products had been removed by suction-filtration, the solution was evaporated to dryness in vacuo. The residue was dissolved in 15 ml of absolute tetrahydrofuran, and the solution was added dropwise, while cooling with ice, to a solution of 87 mg of phosgene (0.88 mmol) in 8.5 ml of tetrahydrofuran. The solution was evaporated in vacuo to about half its volume and, while stirring and cooling with ice, it was added dropwise to a solution of 406 mg of amoxicillin trihydrate in 8 ml of tetrahydrofuran, 2 ml of water and enough triethylamine to give a pH of 8.5 to 8.8.

The reaction mixture was stirred at room temperature for another hour. The pH was maintained at 7.2 to 7.5, if necessary by adding triethylamine. After the addition of 20 ml of water, the tetrahydrofuran was removed in vacuo and, while cooling with ice and stirring, the mixture was adjusted to a pH of 2.5 with 2 N hydrochloric acid. The penicillin thus obtained was suction-filtered off, washed with water and dried in a desiccator in a high vacuum. Yield: 230 mg (38% of theory).

The acid was stirred into a solution of 55 mg of sodium 2-ethylhexanoate in 50 ml of methanol. After some insoluble residue had been filtered off, the sodium salt was precipitated with absolute ether. 160 mg (26% of theory) of the title compound were obtained as a colorless powder.

IR-spectrum: 1760, 1660, 1020 cm$^{-1}$.

NMR-spectrum (DMSO+CD$_3$OD) signals at ppm: 1.55 (d, 6H), 2.95 (m, 2H), 3.75 (m, 2H), 4.05 (s, 1H), 5.45 (m, 3H), 6.75 (d, 2H), 7.30 (d, 2H), 7.80 (q, 4H), 8.40 (s, 1H).

The compounds of the formula

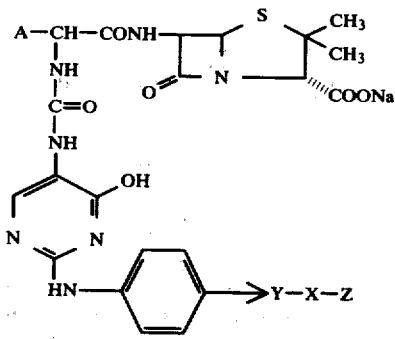

listed in the following table were prepared analogously:

| Example No. | A | →Y—Z—X | IR-Spectrum cm$^{-1}$ | NMR-Spectrum (DMSO + CD$_3$OD) Signals at ppm |
|---|---|---|---|---|
| 35 | HO—◯— | —SO$_2$—CH$_2$CH$_2$—OH | 1765<br>1660<br>1600 | 1.5 (d,6H), 3.5 (m,4H),<br>4.0 (s,1H), 5.4 (m,3H),<br>6.75 (m,2H), 7.2 (m,2H),<br>8.35 (s,1H). |
| 36 | HO—◯— | —SO$_2$—CH$_2$CH$_2$—SO$_2$—CH$_3$ | 1765<br>1660<br>1600<br>1305<br>1140 | 1.55 (d,6H), 3.1 (s,3H),<br>3.5 (m,4H), 4.05 (s,1H),<br>5.4 (m,3H), 6.75 (d,2H),<br>7.25 (d,2H), 7.9 (q,4H),<br>8.4 (s,1H). |
| 37 | HO—◯— | —SO—CH(CH$_3$)(CH$_2$OH) | 1765<br>1655<br>1600 | 0.95 (t,3H), 1.55 (d,6H),<br>2.9 (m,1H), 3.65 (m,2H),<br>4.1 (s,1H), 5.4 (m,3H),<br>6.75 (d,2H), 7.3 (d,2H),<br>7.5 (d,2H), 7.9 (d,2H),<br>8.3 (s,1H). |
| 38 | HO—◯— | —SO—CH$_2$—CH(OH)(CH$_3$) | 1770<br>1660<br>1600 | 1.2 (m,3H), 1.55 (d,6H),<br>2.9 (m,2H), 3.8 (m,1H),<br>4.05 (s,1H), 5.4 (m,3H),<br>6.75 (d,2H), 7.3 (d,2H),<br>7.6 (d,2H), 7.95 (d,2H),<br>8.3 (s,1H). |
| 39 | HO—◯— | —SO—CH$_2$—CH(OH)—CH$_2$—OH | 1765<br>1660<br>1600 | 1.55 (d,6H), 2.95 (m,2H),<br>3.45 (m,3H), 3.65 (m,1H),<br>4.05 (s,1H), 5.4 (m,3H),<br>6.75 (d,2H)<br>7.5 (broad m,4H),<br>8.3 (s,1H), 8.0 (d,2H). |

The compounds of the present invention, that is, those embraced by formulas I and I' and their non-toxic, pharmacologically acceptable salts formed with inorganic or organic bases, have useful pharmacodynamic properties. More particularly, they exhibit antibacterial activity in warm-blooded animals such as mice, and can therefore be used for the prophylaxis and chemotherapy of local and systemic infections in human and veterinary medicine. Examples of diseases which can be prevented or cured with the aid of the compounds of the invention include diseases of the respiratory tract, the pharyngeal cavity and the urinary tract; the compounds are particularly effective against pharyngitis, pneumonia, peritonitis, pyelonephritis, otitis, cystitis, endocarditis, bronchitis, arthritis and general systemic infections.

This utility is made possible by the fact that the compound of the formulas I and I' are extremely effective both in vitro and in vivo against harmful microorganisms, particularly gram-positive and gram-negative bacteria and microorganisms resembling bacteria, and they are distinguished particularly by a broad spectrum of activity.

These penicillin derivatives may be used, for example, to treat and/or prevent local and/or systemic diseases caused by the following pathogens or by mixtures of the following pathogens:

Micrococcaceae, such as Staphylococci;
Lactobacteriaceae, such as Streptococci;
Neisseriaceae, such as Neisseriae;
Corynebacteriaceae, such as *Coryne bacteria;*
Enterobacteriaceae, such as Escherichiae bacteria of the Coli group;
Klebsiella bacteria, such as K. pneumonia;
Proteae bacteria of the Proteus group, such as *Proteus vulgaris;*
Salmonella bacteria, such as Thyphimurium;
Shigella bacteria, such as *Shigella dysenteriae;*
Pseudomonas bacteria, such as *Pseudomonas aeruginosa;*
Aeromonas bacteria, such as *Aeromonas lique faciens;*
Spirillaceae, such as *Vibrio bacteria,* such as *Vibrio cholerae;*
Parvobacteriaceae or Brucellaceae, such as *Pasteurella bacteria;*
Brucella bacteria, such as *Brucella abortus;*
Haemophilus bacteria, such as *Haemophilus influenza;*
Bordetella bacteria, such as *Bordetella pertussis;*
Moraxella bacteria, such as *Moraxella lacunata;*
Bacterioidaceae, such as *Bacteroides bacteria;*
Fusiforme bacteria, such as *Fusobacterium fusiforme;*
Sphaerophorus bacteria, such as *Sphaerophorus necrophorus;*
Bacillaceae, such as aerobic spore formers like *Bacillus anthracis;*
Anaerobic spore-forming Chlostridiae, such as *Chlorstridium perfringens;*
Spirochaetaceae, such as *Borrelia bacteria;*
Treponema bacteria, such as *Treponema pallidum;* and
Leptospira bacteria, such as *Leptospira interrogans.*

The above list of pathogens is purely exemplary and is in no way restrictive.

The following is a list of some typical, particularly effective penicillins according to the invention:

Sodium D-α-{3-[4-hydroxy-2-p-(3',4',5',6'-tetrahydro-pyrimidin-2'-yl)-aminosulfonylanilino-5-pyrimidinyl]-ureido}-p-hydroxybenzyl-penicillin, Sodium D-α-{3-[4-hydroxy-2-p-(4',5'-dihydrooxazol-2'-yl)-amino-sulfonylanilino-5-pyrimidinyl]-ureido}-p-hydroxybenzyl-penicillin, Sodium D-α-{3-[4-hydroxy-2-p-(4',5'-dihydrothiazol-2'-yl)aminosulfonylanilino-5-pyrimidinyl]-ureido}-p-hydroxybenzyl-penicillin, Sodium D-α-{3-[4-hydroxy-2-p-(3',4',5',6'-tetrahydro-pyrimidin-2'-yl)-aminosulfonylanilino-5-pyrimidinyl]-ureido}-benzyl-penicillin, Sodium D-α-{3-[4-hydroxy-2-p-(4',5'-dihydroimidazolyl-2'-yl)-aminosulfonylanilino-5-pyrimidinyl]-ureido}-p-hydroxybenzyl-penicillin, Sodium D-α-{3-[4-hydroxy-2-p-(1'-methyl-3',4',5',6'-tetrahydro-pyrimidin-2'-yl)-aminosulfonylanilino-5-pyrimidinyl]-ureido}-p-hydroxybenzyl-penicillin, Sodium D-α-{3-[4-hydroxy-2-p-(4'-methyl-4',5'-dihydroimidazolyl-2'-yl)-aminosulfonylanilino-5-pyrimidinyl]-ureido}-p-hydroxybenzyl-penicillin, Sodium D-α-[3-[4-hydroxy-2-p-(amino-methylthio)-methylene-imino-sulfonylanilino-5-pyrimidinyl]-ureido}-p-hydroxybenzyl-penicillin, Sodium D-α-{3-[4-hydroxy-2-p-(2'-hydroxyethyl)-sulfinylanilino-5-pyrimidinyl]-ureido}-p-hydroxybenzyl-penicillin, Sodium D-α-{3-[4-hydroxy-2-p-(2'-hydroxyethyl)-sulfinylanilino-5-pyrimidinyl]-ureido}-benzyl-penicillin, Sodium D-α-{3-[4-hydroxy-2-p-(2'-hydroxyisopropyl)-sulfinylanilino-5-pyrimidinyl]-ureido}-p-hydroxybenzyl-penicillin, Sodium D-α-{3-[4-hydroxy-2-p-(2'-hydroxyethylamino)-sulfonylanilino-5-pyrimidinyl]-ureido}-p-hydroxybenzyl-penicillin, Sodium D-α-{3-[4-hydroxy-2-p-(2'-acetylaminoethylamino)-sulfonylanilino-5-pyrimidinyl]-ureido}-p-hydroxybenzyl-penicillin, Sodium D-α-{3-[4-hydroxy-2-p-(aminocarbonylmethylamino)-sulfonylanilino-5-pyrimidinyl]-ureido}-p-hydroxybenzyl-penicillin, and Sodium D-α-{3-[4-hydroxy-2-p-(3'-aminocarbonylpropyl-amino)-sulfonylanilino-5-pyrimidinyl]-ureido}-p-hydroxybenzyl-penicillin.

The antibacterial activity of the β-lactam antibiotics of the present invention was ascertained by the following tests:

1. Tests in vitro

The method of the series dilution test in the microtiter system was used. The substances were tested for bacteriostasis in a liquid medium. The bacteriostatic activity was tested at the following concentrations:

128; 64; 32; 16; 8; 2; 1; 0.5; 0.25; 0.12 and 0.06 μg/ml.

A nutrient medium having the following composition was used: 10 gm of peptone, 8 gm of meat extract oxoid, 3 gm of sodium chloride, and 2 gm of sec. sodium phosphate were made up to 100 ml with distilled water (pH 7.2 to 7.4). The age of the primary cultures was about 20 hours.

The bacterial suspension was adjusted using the photometer (according to "Eppendorf", test tube diameter 14 mm, filter 546 nm) by reference to the turbidity of a barium sulfate comparison suspension which was produced by a barium sulfate suspension formed by the addition of 3.0 ml of 1% barium chloride solution to 97 ml of 1% sulfuric acid. After adjustment, Streptococcus aronson was diluted in the ratio 1:15 and the other test pathogens were diluted in the ratio 1:1500 with a common salt solution.

16 mg of the test substance were weighed in 10 ml measuring flasks and solvent was added up to the mark. Further dilutions in the series were made with distilled water or the solvent in question.

The depressions in the microtiter plates were filled with 0.2 ml of nutrient medium, 0.01 ml of the corresponding diluted substance and a drop of bacterial suspension (0.01 ml) and incubated for 18 to 20 hours at 37° C. A solvent check was carried out continuously at the same time.

The reading was taken macroscopically, and the respective limiting concentration (=the lowest concentration still having bacteriostatic activity) was determined.

The following were used as test organisms:

*Staphylococcus aureus* SG 511, *Escherichia coli* ATCC 11 775, *Pseudomonas aeruginosa* Hamburgensis and *Pseudomonas aeruginosa* BC 19, *Serratia Marcescens* ATCC 13 880, *Klebsiella pneumoniae* ATCC 10 031 and BC 6, *Proteus mirabilis* Hamburgensis, *Proteus rettgeri* BC 7, *Enterobacter cloacae* ATCC 13 047.

Table 1 below lists the minimum inhibitory concentrations (MIC) in μgm/ml determined for typical representatives of the compounds of the present invention. These are the sodium salts of compounds of the formula I where A=p-hydroxyphenyl and R has the indicated meanings.

| R | Compound |
|---|---|
| —NH—⟨C₆H₄⟩—SO₂NH—(N-N-H imidazolyl) | A |
| —NH—⟨C₆H₄⟩—SO₂NH—(N-N-H pyrazolyl) | B |
| —NH—⟨C₆H₄⟩—SO₂NH—(N-S thiazolyl) | C |
| —NH—⟨C₆H₄⟩—SO₂NH—(N-O oxazolyl) | D |
| —NH—⟨C₆H₄⟩—SO₂CH₂CH(OH)CH₃ | E |
| —NH—⟨C₆H₄⟩—SO₂NHCH₂CH₂OH | F |
| —NH—⟨C₆H₄⟩—SO₂NHCH₂CONH₂ | G |
| —NH—⟨C₆H₄⟩—SO₂N(piperazinyl)N—CHO | H |
| compared to azlocillin | J | had an $LD_{50}$ of over 4 gm/kg when administered orally and an $LD_{50}$ of over 2 gm/kg when administered subcutaneously, i.e. no animals died at a dose of 2 gm/kg, and the substances are therefore practically non-toxic.

A number of the compounds of the present invention were tested in vivo against experimental infections in mice. E. coli ATCC 11775 and *Pseudomonas aeruginosa* BC 19 were used as the pathogenic bacteria. An intraperitoneal infection was produced with 0.2 ml of a 5% mucin suspension of the bacteria. This corresponds to about $1.4 \times 10^6$ E. coli bacteria and $1.3 \times 10^6$ Pseudomonas bacteria per mouse. Female mice of the NMRI strain were divided into groups of 10 animals; two groups were untreated, the other groups were treated subcutaneously with various doses of the penicillins of the present invention, to determine the $ED_{50}$ (dose at which 50% of the animals survived). For the E. coli infection, one treatment was given*. For the Pseudomonas infection, three treatments were given (1, 3 and 5 hours post-infectionem).

*1 hour post infectionem

In both cases, the observation period was 7 days. The results of these tests for representatives of the penicillins of the instant invention are shown in Table 2.

TABLE 2

| Compound | E. coli-Infection ED₅₀ (mg/kg) | Compound | Pseud. Infection ED₅₀ (mg/kg) |
|---|---|---|---|
| A | 0.6 | A | 2.1 |
| B | 0.7 | B | 1.9 |
| C | ~3 | C | 17 |
| D | ~2 | E | ~10–20 |
| E | ~2 | F | ~10–20 |
| F | ~5 | | |
| G | ~5 | | |
| J | >100 | J | >100 |

A further object of this invention is to provide pharmaceutical compositions for the treatment of infectious diseases in humans as well as in animals.

The preferred pharmaceutical preparations include tablets, coated tablets, capsules, granulates, suppositories, solutions, suspensions, emulsions, ointments, gels, creams, powders and sprays. Advantageously, the active substance or a mixture of the various active substances of the formulas I and I' is administered, in human or veterinary medicine, at a dose between 5 and 500, preferably 10 to 200 mg/kg body weight per 24 hours, possibly in the form of several single doses. A single dose contains the active ingredient or ingredients according to the invention, preferably in amounts of from about 1 to 250, more particularly 10 to 60 mg/kg

TABLE 1

| Compound | S.aureus SG 511 | E.Coli ATCC 11775 | Pseud. aerug. Hbg. | Pseud. aerug. BC 19 | Serrat. marcesc. ATCC 13880 | Klebs.pneum. ATCC 10031 | Klebs. pneum. BC 6 | Prot. mirabilis Hbg | Prot. rettgeri BC 7 | Eb.cloacae ATCC 13047 |
|---|---|---|---|---|---|---|---|---|---|---|
| A | 0.25 | 0.25 | 1 | 1 | 0.5 | 2 | 2 | 0.06 | 0.5 | 0.5 |
| B | 0.5 | 0.25 | 2 | 1 | 0.25 | 2 | 4 | 0.06 | 0.5 | 0.1 |
| C | 0.25 | 0.12 | 1 | 2 | 0.25 | 1 | 1 | 0.06 | 0.25 | 0.5 |
| D | 0.5 | 0.25 | 1 | 1 | 0.25 | 2 | 4 | 0.06 | 0.25 | 1 |
| E | 0.5 | 0.25 | 1 | 1 | 0.5 | 2 | 2 | 0.03 | 0.5 | 1 |
| F | 0.5 | 0.25 | 2 | 1 | 0.13 | 2 | 4 | 0.06 | 0.5 | 2 |
| G | 0.5 | 0.12 | 1 | 1 | 0.25 | 2 | 2 | 0.06 | 0.5 | 1 |
| H | 0.5 | 0.25 | 2 | 1 | 0.25 | 2 | 2 | 0.06 | 0.5 | 1 |
| J | 0.5 | 8 | 8 | 8 | 4 | 32 | 32 | 2 | 8 | 32 |

The acute toxicity was determined by oral and subcutaneous administration of the compounds of Table 1 in increasing doses to white laboratory mice.

The $LD_{50}$ is the dose which results in the death of 50% of the animals within 8 days. All the substances body weight. However, it may be necessary to deviate from the doses stated above, depending on the nature and body weight of the patient being treated, the nature and gravity of the disease, the type of preparation and the method of administration of the pharmaceutical product and also the period or interval within which the product is administered. Thus, in some cases, it may be adequate to use less than the above-mentioned quantity of active substance, whereas in other cases it may be necessary to use more than the amount of active ingredient specified above. The optimum dose and method of administration of the active ingredients required in each case can readily be determined by anyone skilled in the art based on his or her specialized knowledge.

When used as a feed additive, the novel compounds may be administered at the usual concentrations and in conventional preparations together with the feed or with feed preparations or with drinking water. They thereby prevent, remedy and/or cure infections caused by gram-negative and gram-positive bacteria and also promote growth and bring about an improvement in the utilization of the feed.

For pharmaceutical purposes the compounds of the Formulas I or I' are incorporated as active ingredients into the usual pharmaceutical preparations such as tablets, coated tablets, capsules or ampules. The single dose for adults is generally between 50 and 1000 mg, preferably 100 to 500 mg, while the daily dose is between 100 and 4000 mg, preferably 250 to 2000 mg.

The following examples illustrate a few pharmaceutical compositions comprising a compound of the present invention as an active ingredient and represent the best modes contemplated of using the invention.

EXAMPLE 40

Tablets containing sodium
D-α-{3-[2-p-(2'-hydroxyethyl)sulfinyl-anilino-4-hydroxy-5-pyrimidinyl]-ureido}-p-hydroxybenzyl-penicillin A mixture consisting of 2 kg of active substance, 5 kg of lactose, 1.8 kg of potato starch, 0.1 kg of magnesium stearate and 0.1 kg of talc is compressed in the usual way into tablets, each containing 200 mg of active substance.

EXAMPLE 41

Coated tablets containing
D-α-{3-[2-p-(2'-hydroxyethyl)sulfinyl-anilino-4-hydroxy-5-pyrimidinyl]-ureido}-p-hydroxybenzyl-penicillin Compressed tablets are produced analogous to Example 1 and are then covered in the usual way with a coating consisting of sugar, potato starch, talcum and tragacanth.

EXAMPLE 42

Capsules containing sodium
D-α-{3-[2-p-(2'-hydroxyethyl)sulfinyl-anilino-4-hydroxy-5-pyrimidinyl]-ureido}-p-hydroxybenzyl-penicillin 5 kg of active substance are packaged in hard gelatine capsules in the usual way, each capsule containing 500 mg of the active substance.

EXAMPLE 43

Injectable solution containing sodium
D-α-{3-[4-hydroxy-2-{p-(3',4',5',6'-tetrahydro-pyrimidin-2'-yl)-aminosulfonyl-anilino}-5-pyrimidinyl]-ureido}-p-hydroxybenzyl penicillin Under aseptic conditions, 251 gm of active substance are dissolved in 200 ml of distilled water for injection. The solution is filtered through a millipore filter (pore size 0.22 μm). 2.0 ml portions of the solution are poured into 1000 vials (capacity 10 ml), and the contents are lyophilized. The vials are then sealed with a rubber stopper and an aluminum cover. In this way, vials (No. A) are obtained, each containing 250 mg of active substance.

A physiological saline solution for injection is poured into ampules in portions of 2.0 ml, and the ampules are sealed. In this way, ampules (No. B) are obtained. The physiological saline solution in the ampules (No. B) is poured into the vials (No. A), thus producing an injectable composition suitable for intravenous administration.

Distilled water for injection is poured into the vials (No. A) in amounts of 2.0 ml, and the solution is dissolved in a 5% solution of glucose for injections (250 ml). In this way, solutions for continuous infusion are obtained.

Any one of the other compounds embraced by formulas I and I' or a non-toxic, pharmacologically acceptable salt thereof may be substituted for the particular active ingredient in Examples 40 through 43. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

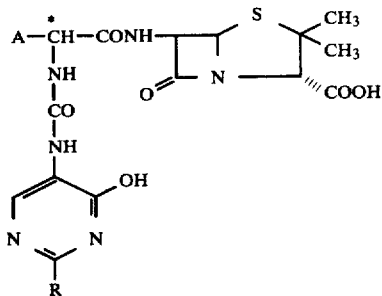

or

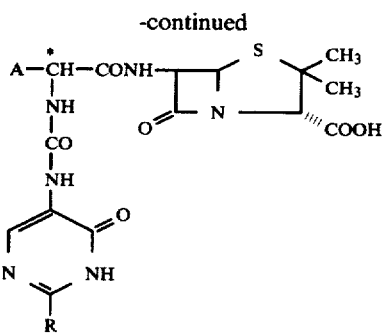

wherein
A is phenyl, 4-hydroxy-phenyl, 2-thienyl or 3,4-dihydroxy-phenyl; and
R is

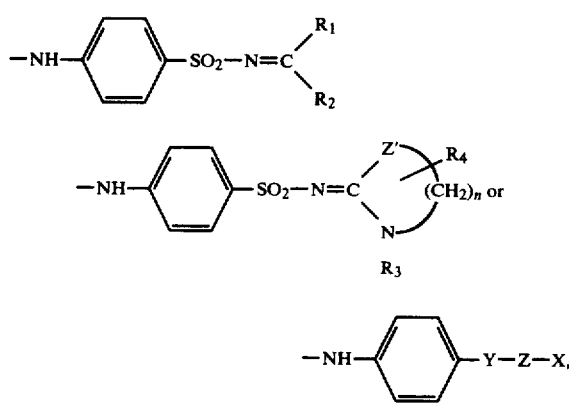

where
$R_1$ and $R_2$ are each methylmercapto or amino;
Z' is oxygen, sulfur or $=NR_3$;
$R_3$ is hydrogen, alkyl of 1 to 3 carbon atoms or hydroxy-(alkyl of 1 to 3 carbon atoms);
$R_4$ is hydrogen, hydroxyl, hydroxymethyl or methyl;
n is 2, 3 or 4;
Y is $-SO_2NH-$, $-SO-$ or $-SO_2-$;
Z is straight or branched alkylene of 1 to 3 carbon atoms;
X is hydroxyl, aminocarbonyl, aminosulfonyl, formylamino, acetylamino, amino, methylsulfinyl, methylsulfonyl or

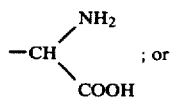; or or
—Y—Z—X is

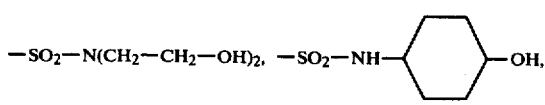

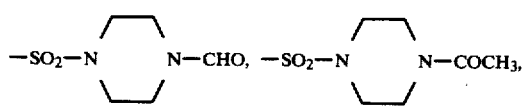

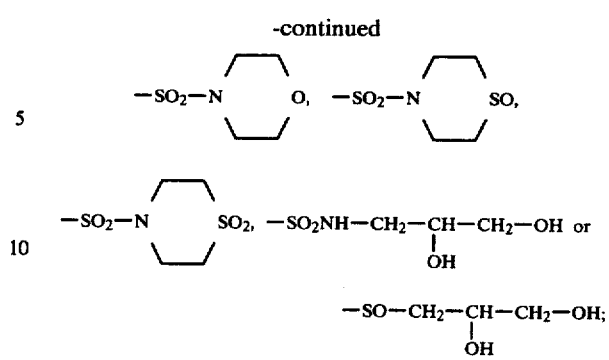

or a non-toxic, pharmacologically acceptable salt thereof formed with an inorganic or organic base.

2. A compound of claim 1 wherein
A is phenyl or p-hydroxy-phenyl; and
R is

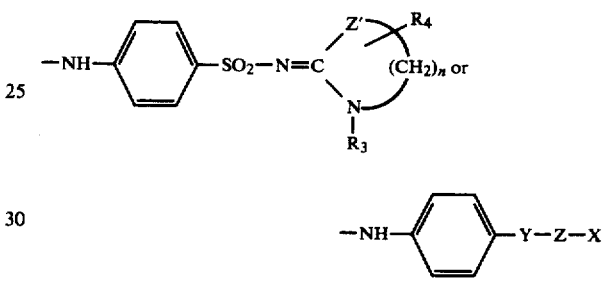

where
n is 2, 3 or 4;
Z' is $=NR_3$;
$R_3$ and $R_4$ are each hydrogen or methyl;
Y and Z have the meanings defined in claim 1;
X is hydroxyl, aminocarbonyl, aminosulfonyl, acetylamino, methylsulfinyl or methylsulfonyl;
or
—Y—Z—X is

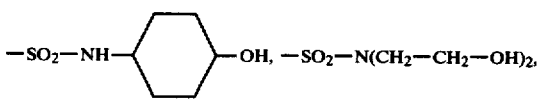

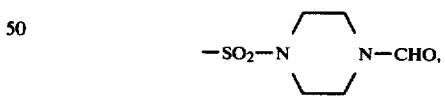

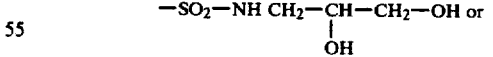

or a non-toxic, pharmacologically acceptable salt thereof formed with an inorganic or organic base.

3. A compound of claim 1 which has the D=R-configuration.

4. A compound of claim 1, which is D-α-{3-[4-hydroxy-2-p-(4',5'-dihydro-oxazol-2'-yl)aminosulfonylanilino-5-pyrimidinyl]-ureido}-p-hydroxybenzylpenicillanic acid or a non-toxic, pharmacologically acceptable salt thereof formed with an inorganic or organic base.

5. A compound of claim 1, which is D-α-{3-[4-hydroxy-2-p-(2'-hydroxy-isopropyl)-sulfinyl-anilino-5-pyrimidinyl]-ureido}-p-hydroxybenzyl-penicillanic acid or a non-toxic, pharmacologically acceptable salt thereof formed with an inorganic or organic base.

6. A compound of claim 1, which is D-α-{3-[4-hydroxy-2-p-(aminocarbonylmethyl-amino)-sulfonyl-anilino-5-pyrimidinyl]-ureido}-p-hydroxybenzyl-penicillanic acid or a non-toxic, pharmacologically acceptable salt thereof formed with an inorganic or organic base.

7. An antibacterial pharmaceutical composition consisting essentially of an inert pharmaceutical carrier and an effective antibiotic amount of a compound of claim 1.

8. The method of inhibiting the growth of or destroying pathogenic bacteria in a warm-blooded animal in need thereof, which comprises perorally, parenterally, rectally or topically administering to said animal an effective antibacterial amount of a compound of claim 1.

* * * * *